US010768317B2

(12) United States Patent
Tateishi

(10) Patent No.: US 10,768,317 B2
(45) Date of Patent: Sep. 8, 2020

(54) RADIOGRAPHIC IMAGE DETECTION DEVICE

(71) Applicant: FUJIFILM Corporation, Tokyo (JP)

(72) Inventor: Masateru Tateishi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/292,718

(22) Filed: Mar. 5, 2019

(65) Prior Publication Data

US 2019/0277982 A1　Sep. 12, 2019

(30) Foreign Application Priority Data

Mar. 6, 2018　(JP) ................. 2018-039376

(51) Int. Cl.
*A61B 6/00*　(2006.01)
*G01T 1/24*　(2006.01)
*G01T 7/00*　(2006.01)
*G03B 42/02*　(2006.01)

(52) U.S. Cl.
CPC ............ *G01T 1/247* (2013.01); *A61B 6/4233* (2013.01); *A61B 6/4283* (2013.01); *A61B 6/505* (2013.01); *G01T 1/244* (2013.01); *G01T 7/00* (2013.01); *G03B 42/02* (2013.01)

(58) Field of Classification Search
CPC ... A61B 6/4208; A61B 6/4233; A61B 6/4283; A61B 6/505; G01T 1/161; G01T 1/202; G01T 1/244; G01T 1/247; G01T 7/00; G03B 42/02
See application file for complete search history.

(56) References Cited

U.S. PATENT DOCUMENTS

| 2011/0215250 A1 | 9/2011 | Ohta et al. |
| 2012/0168632 A1 | 7/2012 | Yagi et al. |
| 2012/0273687 A1* | 11/2012 | Nariyuki ................. G01T 1/244 250/366 |
| 2019/0018151 A1 | 1/2019 | Kawaguchi et al. |

FOREIGN PATENT DOCUMENTS

| JP | 2011-227447 A | 11/2011 |
| JP | 2012-141242 A | 7/2012 |
| JP | 2013-200188 A | 10/2013 |
| JP | 2013200188 A * | 10/2013 |
| WO | WO 2017/145443 A1 | 8/2017 |

OTHER PUBLICATIONS

Extended European Search Report, dated Aug. 5, 2019, for European Application No. 19159932.3.

* cited by examiner

*Primary Examiner* — Mark R Gaworecki
(74) *Attorney, Agent, or Firm* — Birch, Stewart, Kolasch & Birch, LLP

(57) ABSTRACT

A first sensor panel, a second sensor panel, and a base are accommodated in a housing of an electronic cassette. Circuit substrates are mounted on a rear surface of the base. The base is made of a pitch-based carbon fiber reinforced resin obtained by impregnating a pitch-based carbon fiber with a matrix resin. The fiber directions of the pitch-based carbon fibers are aligned with one direction. Therefore, the base has high thermal conductivity in a direction parallel to the fiber direction. As a result, the driving heat of the circuit substrates is rapidly diffused to the entire rear surface.

12 Claims, 12 Drawing Sheets

RADIOGRAPHIC IMAGE DETECTION DEVICE

CROSS-REFERENCE TO RELATED APPLICATIONS

This application claims priority under 35 U.S.C § 119 (a) to Japanese Patent Application No. 2018-039376 filed on 6 March 2018. The above application is hereby expressly incorporated by reference, in its entirety, into the present application.

BACKGROUND OF THE INVENTION

1. Field of the Invention

The present invention relates to a radiographic image detection device.

2. Description of the Related Art

In a medical field, a diagnosis is made on the basis of a radiographic image detected by a radiographic image detection device. The radiographic image detection device comprises a sensor panel, a circuit unit, and a base. In the sensor panel, a plurality of pixels that accumulate charge in response to radiation which has been emitted from a radiation source and then transmitted through a subject (patient) are two-dimensionally arranged. The radiographic image detection device comprising the sensor panel is also called a flat panel detector (FPD). The circuit unit converts the charge accumulated in the pixels of the sensor panel into a digital signal and outputs the digital signal as a radiographic image. The circuit unit includes a plurality of circuit substrates on which various circuits are mounted. The base has a front surface to which the sensor panel is attached and a rear surface on which the circuit substrates are mounted.

Heat is generated from a circuit substrate by the driving of various circuits. JP2013-200188A discloses a radiographic image detection device in which a base having a front surface to which a sensor panel is attached and a rear surface on which a circuit substrate is mounted is used as a heat insulating structure, which makes it difficult for the driving heat of the circuit substrate to be transferred to the sensor panel through the base. Specifically, the base includes two plates and an internal portion interposed between the two plates. The internal portion has a honeycomb structure in which columnar spaces formed by cell walls of regular hexagonal columns are arranged without a gap therebetween. A thermal conduction path in the honeycomb structure is narrower than that in a solid structure. Therefore, it is possible to significantly reduce the amount of driving heat transferred to the sensor panel.

SUMMARY OF THE INVENTION

Some circuit substrates generate a relatively large amount of driving heat and others generate a relatively small amount of driving heat. In addition, there are various circuit substrates having different sizes or shapes and there are various layouts of the circuit substrates on the rear surface of the base. Therefore, a temperature distribution in the rear surface of the base is not uniform and the rear surface of the base has a portion that is locally heated and another portion that is not locally heated. In a case in which heat with a non-uniform temperature distribution is transferred to the sensor panel through the base and the sensor panel is locally heated, local density unevenness occurs in a radiographic image and the quality of the radiographic image is degraded.

In JP2013-200188A, the base is used as the heat insulating structure and driving heat unlikely to be transferred in the thickness direction. However, there are no measures for the degradation of the quality of a radiographic image caused by a non-uniform temperature distribution in the rear surface of the base.

An object of the invention is to provide a radiographic image detection device that can reduce the possibility that a sensor panel will be locally heated by the driving heat of a circuit substrate and can suppress the degradation of the quality of a radiographic image.

In order to solve the problems, according to the invention, there is provided a radiographic image detection device comprising: a sensor panel in which pixels that accumulate charge in response to radiation, which has been emitted from a radiation source and transmitted through a subject, are two-dimensionally arranged; a circuit unit that converts the charge into a digital signal, outputs the digital signal as a radiographic image, and includes a plurality of circuit substrates on which various circuits are mounted; and a base that has a front surface to which the sensor panel is attached and a rear surface on which the circuit substrates are mounted and has anisotropic thermal conductivity in at least the rear surface.

Preferably, at least one of the plurality of circuit substrates has a rectangular shape in a plan view and is provided such that a long side direction is perpendicular to a direction in which thermal conductivity is high in the rear surface. In this case, preferably, a length of a long side of the circuit substrate is equal to or greater than a quarter of a length of a side of the base along the long side direction.

Preferably, the rear surface is divided into two equal regions, that is, a high-density region in which mounting density of the circuit substrates is relatively high and a low-density region in which the mounting density of the circuit substrates is relatively low and the circuit substrates are provided in the high-density region and the low-density region. Preferably, in the rear surface, thermal conductivity in a direction from the high-density region to the low-density region is high.

Preferably, the rear surface is divided into two equal regions, that is, a high-temperature region in which an amount of heat generated from the circuit substrates is relatively large and a low-temperature region in which the amount of heat generated from the circuit substrates is relatively small and the circuit substrates are provided in the high-temperature region and the low-temperature region. Preferably, in the rear surface, thermal conductivity in a direction from the high-temperature region to the low-temperature region is high.

Preferably, the base includes a pitch-based carbon fiber reinforced resin obtained by impregnating a pitch-based carbon fiber with a matrix resin. Preferably, at least the rear surface of the base is made of the pitch-based carbon fiber reinforced resin. Alternatively, preferably, a sheet that is made of a pitch-based carbon fiber reinforced resin obtained by impregnating a pitch-based carbon fiber with a matrix resin is attached to the rear surface of the base. In these cases, preferably, fiber directions of the pitch-based carbon fibers are aligned with one direction.

Preferably, a heat insulating member is attached to the front surface of the base and the sensor panel is attached to the front surface through the heat insulating member.

Preferably, two pairs each including the sensor panel and the circuit unit are provided and the two sensor panels are sequentially arranged in a thickness direction. In this case, preferably, two radiographic images output from the two circuit units are used to calculate an index value related to bones.

According to the invention, the base having the front surface to which the sensor panel is attached and the rear surface on which the circuit substrates of various circuits are mounted has anisotropic thermal conductivity in at least the rear surface. Therefore, it is possible to provide a radiographic image detection device that can reduce the possibility that a sensor panel is locally heated by the driving heat of a circuit substrate and can suppress the degradation of the quality of a radiographic image.

DESCRIPTION OF THE PREFERRED EMBODIMENTS

First Embodiment

Figure 1:
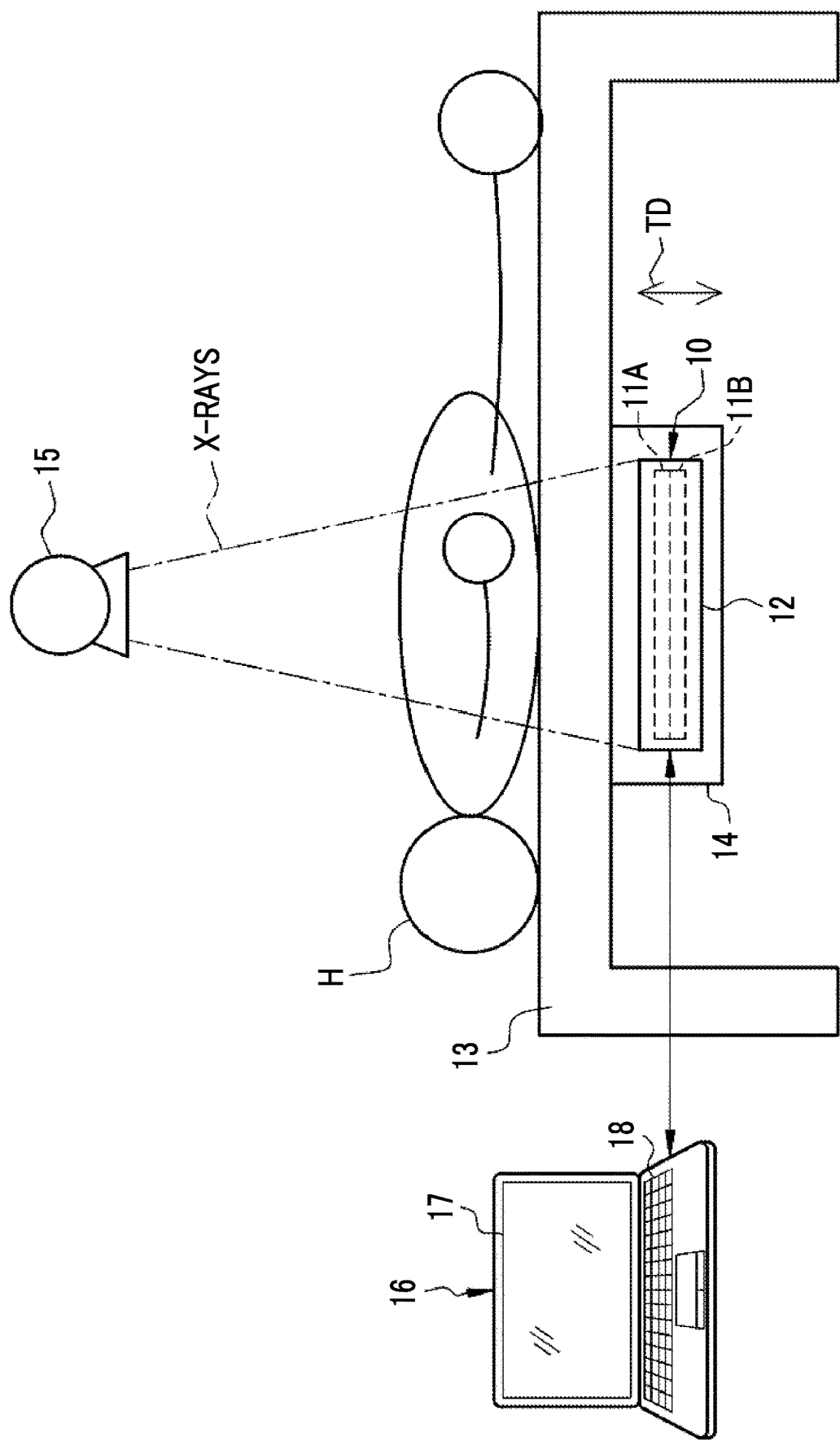
FIG. 1 is a diagram illustrating an aspect of X-ray imaging.

In FIG. 1, an electronic cassette 10 corresponding to a radiographic image detection device according to the invention has a first sensor panel 11A and a second sensor panel 11B which are accommodated in a housing 12. The first and second sensor panels 11A and 11B are thin plates having a rectangular shape in a plan view and are sequentially arranged in a thickness direction TD.

The housing 12 is a portable box having a rectangular parallelepiped shape and has a size which is based on the International Organization for Standardization (ISO) 4090: 2001 and is substantially equal to the size of, for example, a film cassette, an imaging plate (IP) cassette, or a computed radiography (CR) cassette. The housing 12 is made of a conductive material, such as a resin mixed with carbon fibers, a resin mixed with an aluminum or nickel filler, an aluminum alloy, or a magnesium alloy.

The electronic cassette 10 is set in a holder 14 of an imaging table 13 on which a subject H lies supine. Then, the electronic cassette 10 receives X-rays (represented by a one-dot chain line) corresponding to radiation which has been emitted from an X-ray source 15 corresponding to a radiation source and then transmitted through the subject H and detects an X-ray image corresponding to a radiographic image.

The electronic cassette 10 is connected to a console 16 and communicates with the console 16 to transmit and receive various kinds of information. Various kinds of information include, for example, the X-ray images detected by the electronic cassette 10 and an imaging menu input by an operator through the console 16. The imaging menu is, for example, a set of an imaging part, such as the head or the chest, a posture, such as an upright position, a lying position, or a sitting position, and the orientation of the subject H with respect to X-rays, such as the front, the side, or the back.

For example, the console 16 is configured by installing a control program, such as an operating system, and various application programs in a computer such as a notebook personal computer. The console 16 includes a display 17 and an input device 18 such as a touch pad or a keyboard. For example, the X-ray image transmitted from the electronic cassette 10 is displayed on the display 17.

Figure 2:
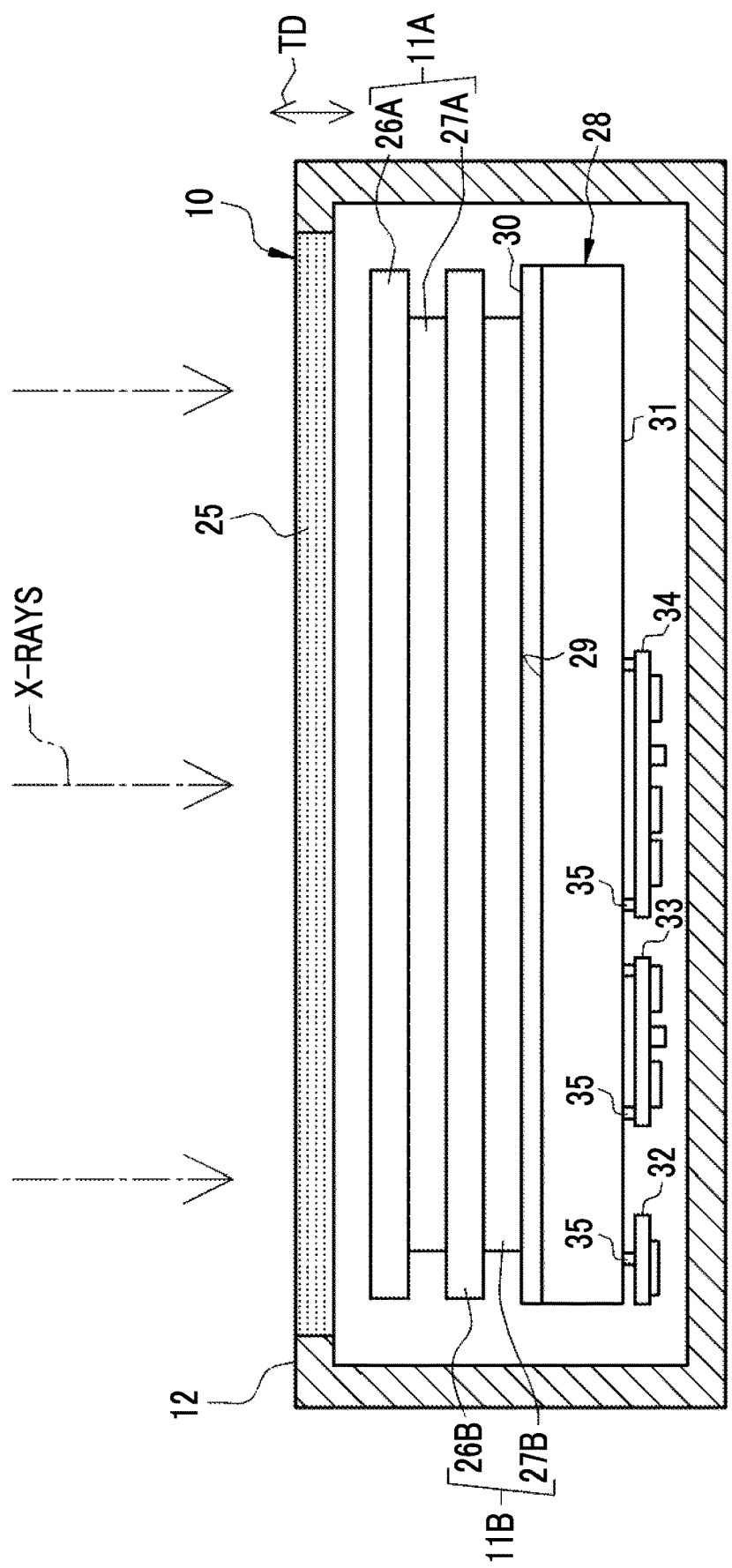
FIG. 2 is a diagram illustrating the internal structure of an electronic cassette.

In FIG. 2, a rectangular opening is formed in a front surface of the housing 12 on which X-rays are incident and a transmission plate 25 that transmits X-rays is attached to the opening. The first sensor panel 11A and the second sensor panel 11B are provided immediately below the transmission plate 25. Here, the thickness direction TD in which the first and second sensor panels 11A and 11B are sequentially arranged is a direction that is parallel to a line normal to the front surface of the housing 12 and a rear surface of the housing 12 opposite to the front surface. The first sensor panel 11A includes a first light detection substrate 26A and a first scintillator 27A. The first light detection substrate 26A and the first scintillator 27A are arranged in the order of the first light detection substrate 26A and the first scintillator 27A as viewed from the front surface of the housing 12 on which X-rays are incident. Similarly, the second sensor panel 11B includes a second light detection substrate 26B and a second scintillator 27B which are arranged in the order of the second light detection substrate 26B and the second scintillator 27B as viewed from the front surface of the housing 12. In addition, a sensor panel in which a scintillator 27 and a light detection substrate 26 are sequentially arranged as viewed from the front surface of the housing 12 may be used. Further, a direct-conversion-type sensor panel that directly converts X-rays into charge with a photoconductive film made of, for example, amorphous selenium may be used.

The first scintillator 27A has a phosphor, such as CsI:Tl (thallium-activated cesium iodide), and the second scintillator 27B has a phosphor, such as GOS ($Gd_2O_2S$:Tb, terbium-activated gadolinium oxysulfide). Each of the first and second scintillators 27A and 27B converts incident X-rays into visible light and emits the visible light. The first and second light detection substrates 26A and 26B detect the visible light emitted from the first and second scintillators 27A and 27B and convert the visible light into charge.

The housing 12 accommodates a base 28 in addition to the first and second sensor panels 11A and 11B. A heat insulating member 30 having a sheet shape is attached to a front surface (a surface on which X-rays are incident) 29 of the base 28. The first and second sensor panels 11A and 11B are attached to the front surface 29 of the base 28 through the heat insulating member 30. The heat insulating member 30 is, for example, a sponge sheet. In contrast, three circuit substrates 32, 33, and 34 provided with various circuits are mounted and fixed to a rear surface (a surface opposite the front surface 29) 31 of the base 28 through spacers 35 that are made of metal.

The base 28 is fixed to the inner surface of the housing 12 by, for example, a resin adhesive. The housing 12 accommodates a cable connector (not illustrated) that performs wired communication with the console 16 and receives power from a commercial power supply in addition to these components. The housing 12 may accommodate an antenna for wireless communication with the console 16 and a battery for wirelessly driving the electronic cassette 10.

Figure 3:
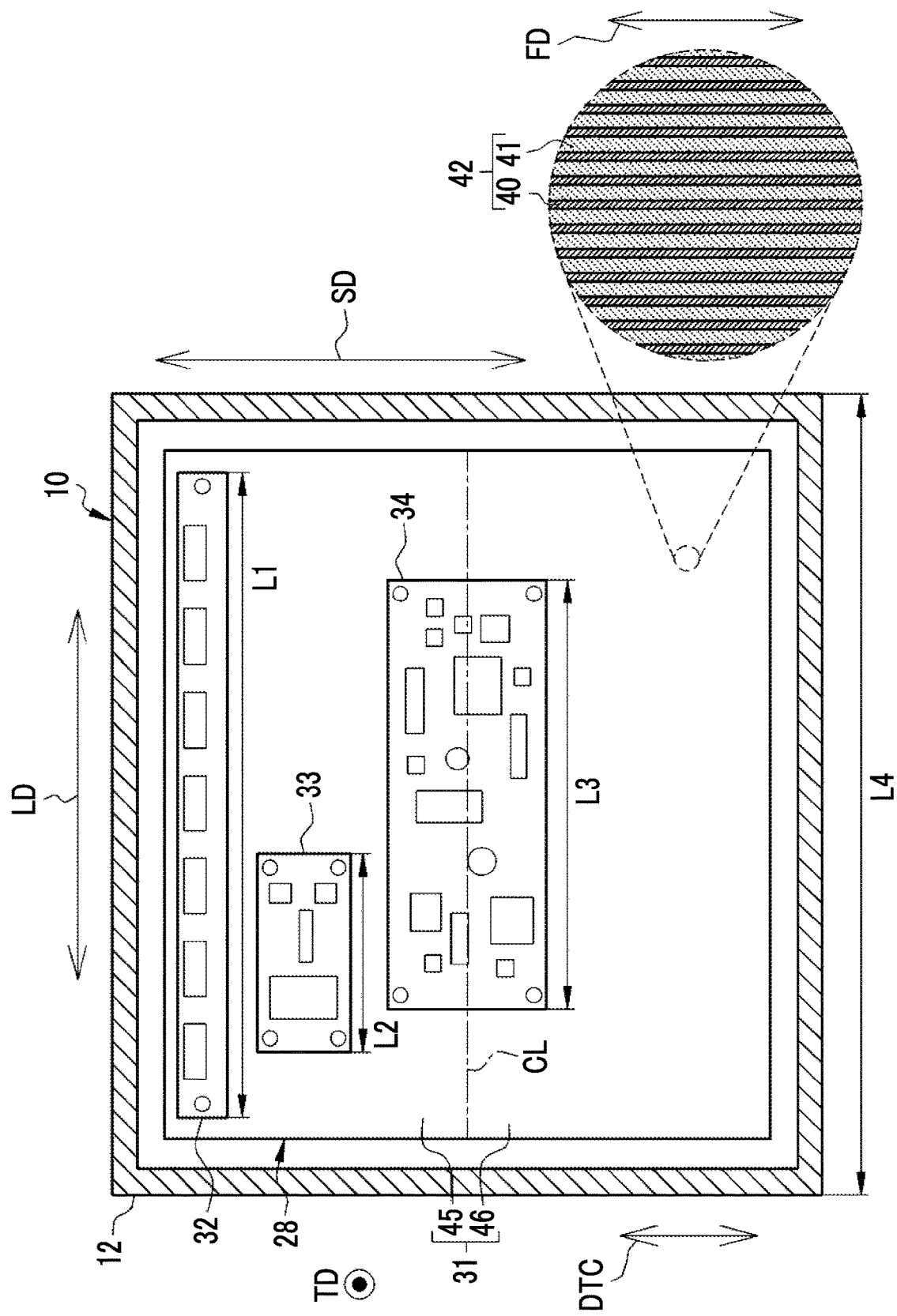
FIG. 3 is a plan view illustrating a base as viewed from a rear surface of a housing.

In FIG. 3 which is a plan view of the base 28 as viewed from the rear surface of the housing 12, the circuit substrates 32 to 34 are arranged such that they are close to each other and are biased to one side (the upper side in FIG. 3) of the rear surface 31 of the base 28. All of the circuit substrates 32 to 34 have a rectangular shape in a plan view and are arranged such that the long side directions LD thereof are aligned with each other and the short side directions SD thereof are aligned with each other.

The base 28 is made of a pitch-based carbon fiber reinforced resin 42 obtained by impregnating a pitch-based carbon fiber 40 with a matrix resin 41, as illustrated in a dashed circle. As is well known, the pitch-based carbon fiber 40 is obtained by carbonizing a pitch precursor such as coal tar or heavy petroleum.

The fiber directions FD of the pitch-based carbon fibers 40 are aligned with one direction. Since the pitch-based carbon fiber 40 has a higher thermal conductivity than the matrix resin 41, heat is likely to be transferred in the fiber direction FD. Therefore, in a case in which the fiber directions FD of the pitch-based carbon fibers 40 are aligned with one direction, the pitch-based carbon fiber reinforced resin 42 has a high thermal conductivity in the fiber direction FD. Since the base 28 is made of the pitch-based carbon fiber reinforced resin 42, the base 28 has anisotropic thermal conductivity. Specifically, the base 28 has high thermal conductivity in a direction DTC parallel to the fiber direction FD.

The circuit substrates 32 to 34 are arranged such that the long side direction LD is perpendicular to the direction DTC (the short side direction SD is parallel to the direction DTC). In addition, the lengths L1, L2, and L3 of the long sides of the circuit substrates 32 to 34 are equal to or greater than a quarter of the length L4 of a side of the base 28 along the long side direction LD (L1, L2, and L3≥(1/4)×L4).

As described above, the circuit substrates 32 to 34 are arranged so as to be biased to one side of the rear surface 31. Therefore, the rear surface 31 is divided into two equal regions, that is, a high-density region 45 in which the mounting density of the circuit substrates is relatively high and a low-density region 46 in which the mounting density of the circuit substrates is relatively low by a center line CL represented by a one-dot chain line. Specifically, the circuit substrates 32 and 33 and half of the circuit substrate 34 are provided in the high-density region 45 and only the other half of the circuit substrate 34 is provided in the low-density region 46.

Most of the circuit substrates 32 to 34 are provided in the high-density region 45 and only half of the circuit substrate 34 is provided in the low-density region 46. Therefore, the high-density region 45 corresponds to a high-temperature region in which the amount of heat generated from the circuit substrates is relatively large and the low-density region 46 corresponds to a low-temperature region in which the amount of heat generated from the circuit substrates is relatively small.

The direction DTC of the rear surface 31 in which thermal conductivity is high is a direction from the high-density and high-temperature region 45 to the low-density and low-temperature region 46. Therefore, the rear surface 31 has high thermal conductivity in the direction from the high-density region to the low-density region and has high thermal conductivity in the direction from the high-temperature region to the low-temperature region.

The mounting density of the circuit substrates literally means the percentage of the area of the circuit substrates in each of the two equally divided regions of the rear surface 31. The amount of heat generated from the circuit substrates specifically means the maximum temperature of the driving heat of the circuit substrate.

The relatively large or small amount of heat generated from the circuit substrate is the comparison result of the sum of the amounts of heat generated from the provided circuit substrates. That is, in a case in which the sum of the amounts of heat generated from the circuit substrates provided in one of the two equally divided regions of the rear surface 31 is larger than the sum of the amounts of heat generated from the circuit substrates provided in the other region, the one region is the high-temperature region and the other region is the low-temperature region. Therefore, in a case in which one circuit substrate is provided in the one region, four circuit substrates are provided in the other region, and the amount of heat generated from the one circuit substrate provided in the one region is larger than the sum of the amounts of heat generated from the four circuit substrates provided in the other regions, the one region is the high-temperature region and the other region is the low-temperature region. That is, the distinction between the high-temperature region and the low-temperature region does not depend on the number of circuit substrates provided and is determined by the sum of the amounts of heat generated from the circuit substrates provided.

Figure 4:
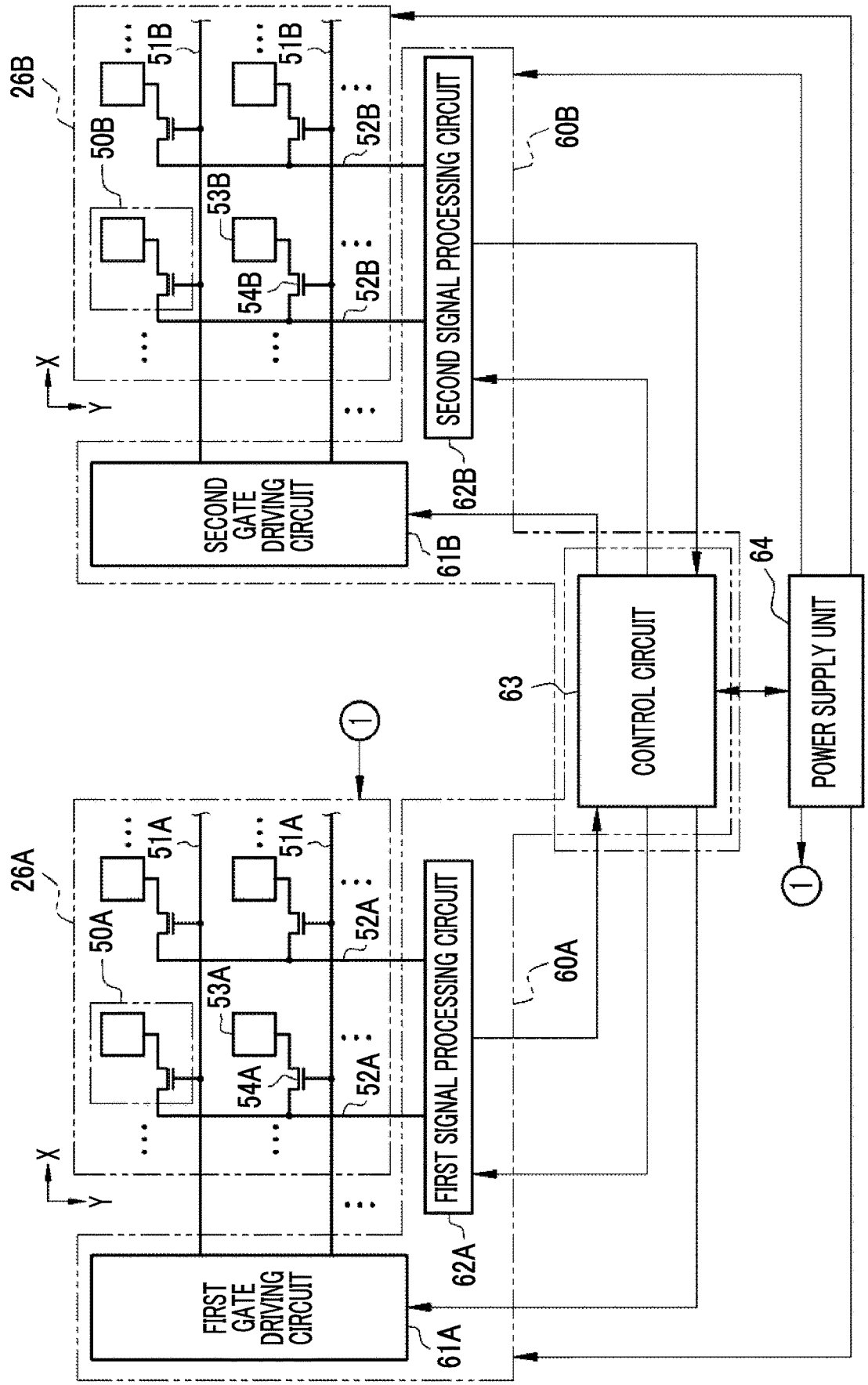
FIG. 4 is a block diagram illustrating the electrical configuration of the electronic cassette.

In FIG. 4, the first light detection substrate 26A is configured by providing first pixels 50A which are arranged in a two-dimensional matrix of N rows and M columns, N first gate lines 51A, and M first signal lines 52A on a glass substrate (not illustrated). The first gate lines 51A extend in the X direction along a row direction of the first pixels 50A and are arranged at a predetermined pitch in the Y direction along a column direction of the first pixels 50A. The first signal lines 52A extend in the Y direction and are arranged at a predetermined pitch in the X direction. The first gate lines 51A and the first signal lines 52A are orthogonal to each other and the first pixels 50A are provided so as to correspond to the intersection points between the first gate lines 51A and the first signal lines 52A.

N and M are integers that are equal to or greater than 2. For example, N is 2880 and M is 2304. In addition, the array of the first pixels 50A may be a square array as illustrated in FIG. 4. The first pixels 50A may be inclined at 45° and may be arranged in zigzag.

As is well known, the first pixel 50A comprises a first photoelectric conversion unit 53A on which visible light is incident and which generates charge (electron-hole pair) and accumulates the charge and a first thin film transistor (TFT) 54A. The first photoelectric conversion unit 53A has a structure in which an upper electrode and a lower electrode are provided on the upper and lower sides of a semiconductor layer that generates charge. The semiconductor layer is, for example, a p-intrinsic-n (PIN) type and includes an N-type layer provided on the upper electrode side and a P-type layer provided on the lower electrode side. The first TFT 54A has a gate electrode connected to the first gate line 51A, a source electrode connected to the first signal line 52A, and a drain electrode connected to the lower electrode of the first photoelectric conversion unit 53A. In addition, a light detection substrate that is not a TFT type, but is a complementary metal oxide semiconductor (CMOS) type may be used.

A bias line (not illustrated) is connected to the upper electrode of the first photoelectric conversion unit 53A. A positive bias voltage is applied to the upper electrode through the bias line. The positive bias voltage is applied to generate an electric field in the semiconductor layer. Therefore, in the electron-hole pair generated in the semiconductor layer by photoelectric conversion, the electron is moved to the upper electrode and is absorbed by the bias line and the hole is moved to the lower electrode and is collected as charge.

The second light detection substrate 26B has the same configuration as the first light detection substrate 26A. Therefore, alphabet "B" is added next to numbers for components of the second light detection substrate 26B to distinguish the components from the components of the first light detection substrate 26A and the description of the components will not be repeated.

Various circuits mounted on the circuit substrates 32 to 34 belong to a first circuit unit 60A or a second circuit unit 60B. The first circuit unit 60A is for the first sensor panel 11A. In addition, the second circuit unit 60B is for the second sensor panel 11B. That is, there are two pairs of the sensor panels and the circuit units, that is, a pair of the first sensor panel 11A and the first circuit unit 60A and a pair of the second sensor panel 11B and the second circuit unit 60B.

The first circuit unit 60A includes a first gate driving circuit 61A, a first signal processing circuit 62A, and a control circuit 63. The second circuit unit 60B includes a second gate driving circuit 61B, a second signal processing circuit 62B, and the control circuit 63. That is, the control circuit 63 is shared by the first and second circuit units 60A and 60B.

The first gate driving circuit 61A is connected to the ends of the first gate lines 51A and generates a gate pulse for driving the first TFTs 54A. The control circuit 63 drives the first TFTs 54A through the first gate driving circuit 61A and controls the driving of the first signal processing circuit 62A to control the operation of the first sensor panel 11A. Specifically, the control circuit 63 directs the first sensor panel 11A to perform a pixel reset operation which reads dark charge from the first pixel 50A and resets (removes) the dark charge, a pixel charge accumulation operation which accumulates charge corresponding to the amount of X-rays reaching the first pixel 50A in the first pixel 50A, and an image reading operation which reads the charge accumulated in the first pixel 50A to the first signal processing circuit 62A through the first signal line 52A.

The first signal processing circuit 62A converts the accumulated charge read from the first pixel 50A by the image reading operation into an analog voltage signal. Then, the first signal processing circuit 62A performs a known correlated double sampling process for the analog voltage signal to remove a noise component from the analog voltage signal. Then, the first signal processing circuit 62A converts the analog voltage signal into a digital signal corresponding to the voltage value of the analog voltage signal (analog/digital conversion) and outputs the digital signal to the control circuit 63. The control circuit 63 stores the digital signal output from the first signal processing circuit 62A as an X-ray image (a first X-ray image, see FIG. 5) in an embedded memory (not illustrated). In addition, the second circuit unit 60B has the same configuration as the first circuit unit 60A. Therefore, as in the case of the second light detection substrate 26B, the description of the second circuit unit 60B is omitted.

A power supply unit 64 supplies power to the first and second sensor panels 11A and 11B and the first and second circuit units 60A and 60B under the control of the control circuit 63. The power supply unit 64 is provided with a switching power supply. The switching power supply converts a voltage based on power from a battery or a commercial power supply into a voltage suitable for the first and second sensor panels 11A and 11B and the first and second circuit units 60A and 60B using a pulse modulation method, for example, a pulse width modulation (PWM) method, and outputs the voltage.

Figure 5:
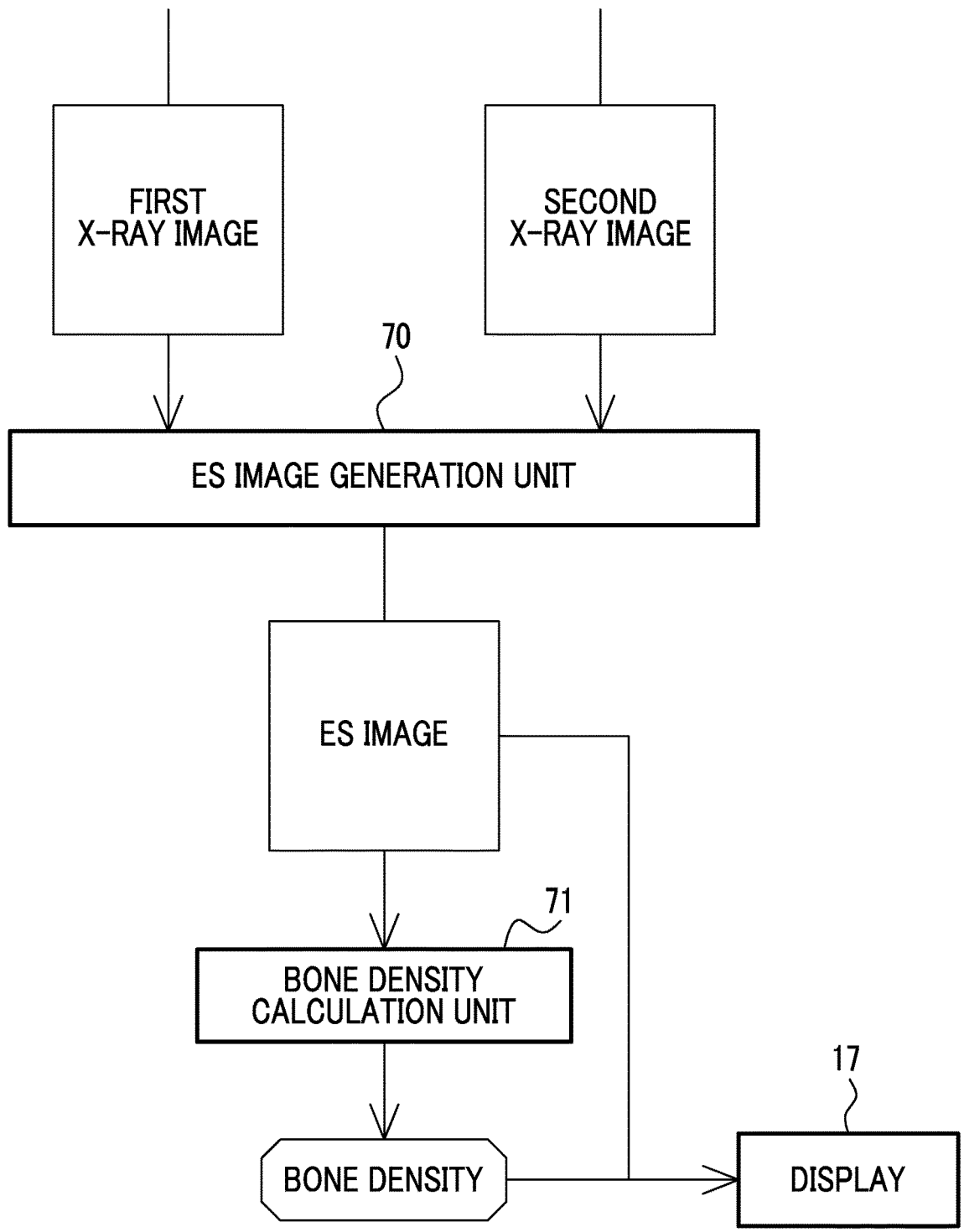
FIG. 5 is a block diagram illustrating the configuration of a console related to the calculation of bone density.

In FIG. 5, the console 16 receives a first X-ray image from the first sensor panel 11A and receives a second X-ray image from the second sensor panel 11B. The first X-ray image and the second X-ray image are based on the charge accumulated in the first and second pixels 50A and 50B in response to the X-rays which have been emitted from the X-ray source 15 and then transmitted through the subject H, respectively, and indicate the internal structure of the body of the subject H.

An offset correction process which removes artifacts caused by fixed pattern noise which is an example of noise caused by the usage environment of the electronic cassette 10, such as environmental temperature, is performed for the first X-ray image and the second X-ray image and then the first X-ray image and the second X-ray image are input to an ES image generation unit 70. The ES image generation unit 70 generates an ES image from the first X-ray image and the second X-ray image. Specifically, the ES image generation unit 70 subtracts an image obtained by multiplying the first X-ray image by a predetermined coefficient from an image obtained by multiplying the second X-ray image by a predetermined coefficient in units of pixels. The ES image generated by the subtraction process is, for example, an image in which soft tissues have been removed and bone tissues have been highlighted.

A bone density calculation unit 71 calculates bone density in an imaging part of the subject H as an index value related to bones. Specifically, first, the bone density calculation unit 71 analyzes the ES image from the ES image generation unit 70 to extract a bone tissue region of the ES image. Then, for example, the bone density calculation unit 71 multiplies a representative value (for example, the mean, maximum value, or mode) of the pixel values of the bone tissue region by a conversion coefficient for converting the pixel values into a bone mass to calculate the bone mass. The bone density calculation unit 71 divides the calculated bone mass by the area of the bone tissue region to calculate bone density.

The console 16 displays, for example, the bone density calculated by the bone density calculation unit 71 and the ES image generated by the ES image generation unit 70 on the display 17. As such, the X-ray images output from the first and second sensor panels 11A and 11B are used to calculate the index value related to bones. Further, in addition to or instead of the bone density, the bone mass may be displayed on the display 17.

For example, an application program related to X-ray imaging is executed to construct the ES image generation unit 70 and the bone density calculation unit 71 in a central processing unit (CPU) of the console 16. Some or all of the above-mentioned units may be constructed in the CPU of the electronic cassette 10 and the electronic cassette 10 may perform the generation of the ES image or the calculation of bone density.

Next, the operation of the above-mentioned configuration will be described. In a case in which X-ray imaging is performed for the subject H using the electronic cassette 10, the operator turns on the electronic cassette 10 and sets the electronic cassette 10 in the holder 14 of the imaging table 13. Then, the operator adjusts the positional relationship among the electronic cassette 10, the X-ray source 15, and the subject H and then operates the X-ray source 15 to emit X-rays.

The X-rays which have been emitted from the X-ray source 15 and then transmitted through the subject H are incident on the first sensor panel 11A and the second sensor panel 11B through the transmission plate 25. Each of the first and second sensor panels 11A and 11B receives the emitted X-rays and sequentially performs the pixel reset operation and the pixel charge accumulation operation. The charge corresponding to the amount of X-rays reaching each of the first and second pixels 50A and 50B is accumulated in each of the first and second pixels 50A and 50B.

After the emission of the X-rays ends, the image reading operation is performed in each of the first and second sensor panels 11A and 11B. Then, the first X-ray image and the second X-ray image are output from the first sensor panel 11A and the second sensor panel 11B, respectively.

In a case in which the first and second sensor panels 11A and 11B perform various operations, the circuit substrates 32 to 34 included in the first and second circuit units 60A and 60B generate heat. The driving heat of the circuit substrates 32 to 34 is transferred to the rear surface 31 of the base 28 on which the circuit substrates 32 to 34 are mounted through the spacers 35.

As illustrated in FIG. 3, the base 28 is made of the pitch-based carbon fiber reinforced resin 42 obtained by impregnating the pitch-based carbon fiber 40 with the matrix resin 41, the fiber directions FD of the pitch-based carbon fibers 40 are aligned with one direction, and thermal conductivity in the direction DTC parallel to the fiber direction FD is high. Therefore, the driving heat of the circuit substrates 32 to 34 transferred to the rear surface 31 of the base 28 is rapidly diffused to the entire rear surface 31 along the direction DTC and the rear surface 31 of the base 28 immediately changes to a thermal equilibrium state. Therefore, it is possible to reduce the possibility that the rear surface 31 of the base 28 and the first and second sensor panels 11A and 11B attached to the front surface 29 of the base 28 will be locally heated by the driving heat of the circuit substrates 32 to 34. Therefore, it is possible to solve the problem that local density unevenness occurs in each X-ray image and the quality of each X-ray image is degraded.

In addition, the circuit substrates 32 to 34 having a rectangular shape in a plan view are arranged such that the long side directions LD thereof are perpendicular to the direction DTC. Therefore, a large amount of driving heat of the circuit substrates 32 to 34 can be diffused not from a narrow short side but from a wide long side and it is possible to increase the speed at which the rear surface 31 of the base 28 changes to the thermal equilibrium state.

The lengths L1, L2, and L3 of the long sides of the circuit substrates 32 to 34 are equal to or greater than a quarter of the length L4 of the side of the base 28 along the long side direction LD. Therefore, it is possible to diffuse the driving heat of the circuit substrates 32 to 34 to a wider region and to effectively prevent each of the first and second sensor panels 11A and 11B from being locally heated. In contrast, in a case in which the lengths L1, L2, and L3 of the long sides of the circuit substrates 32 to 34 are less than a quarter of the length L4 of the side of the base 28 along the long side direction LD, the effect of diffusing the driving heat of the circuit substrates 32 to 34 is limited by anisotropy imparted to the thermal conductivity of the rear surface 31. In addition, it is preferable that the lengths of the long sides of the circuit substrates are equal to or greater than half of the side of the base 28 along the long side direction LD.

The rear surface 31 is divided into two equal regions, that is, the high-density and high-temperature region 45 in which the amount of heat generated from the circuit substrates is relatively large and the mounting density of the circuit substrates is relatively high and the low-density and low-temperature region 46 in which the amount of heat generated from the circuit substrates is relatively small and the mounting density of the circuit substrates is relatively low. In addition, thermal conductivity in the direction from the high-density and high-temperature region 45 to the low-density and low-temperature region 46 is high. Therefore, it is possible to effectively diffuse driving heat from the high-density and high-temperature region 45 to the low-density and low-temperature region 46 and to further increase the speed at which the rear surface 31 of the base 28 changes to the thermal equilibrium state.

The heat insulating member 30 is attached to the front surface 29 of the base 28 and the first and second sensor panels 11A and 11B are attached to the front surface 29 of the base 28 through the heat insulating member 30. Therefore, it is possible to effectively prevent the driving heat of the circuit substrates 32 to 34 transferred to the rear surface 31 of the base 28 from being transferred to each of the first and second sensor panels 11A and 11B.

In the first and second sensor panels 11A and 11B, the first and second light detection substrates 26A and 26B and the first and second scintillators 27A and 27B are arranged in this order, respectively, as viewed from the front surface of the housing 12 on which X-rays are incident. Therefore, the driving heat of the circuit substrates 32 to 34 is less likely to be transferred to the first and second light detection substrates 26A and 26B than that in a case in which the first and second scintillators 27A and 27B and the first and second light detection substrates 26A and 26B are arranged in this order.

Each X-ray image is transmitted from the electronic cassette 10 to the console 16. In the console 16, as illustrated in FIG. 5, the ES image generation unit 70 generates an ES image and the bone density calculation unit 71 calculates bone density on the basis of the ES image. The bone density is displayed on the display 17 together with, for example, the ES image.

In a case in which the quality of the X-ray image which is the origin of the calculation of the index value related to bones, such as bone density, is not guaranteed, there is a concern that the reliability of the index value will be significantly reduced. However, in the invention, since the quality of the X-ray image is guaranteed at a relatively high level, it is possible to improve the reliability of the index value.

In the configuration in which the first and second sensor panels 11A and 11B are sequentially arranged in the thickness direction, the amount of radiation reaching the second sensor panel 11B is reduced to 10% to 20% of the amount of radiation reaching the first sensor panel 11A. Therefore, the signal-noise (SN) ratio of the second X-ray image is reduced. In a case in which the second sensor panel 11B is locally heated by the driving heat of the circuit substrates 32 to 34 and local density unevenness occurs in the second X-ray image, the influence of the driving heat is relatively large. Therefore, the invention is effective in the configuration in which the first and second sensor panels 11A and 11B are sequentially arranged in the thickness direction.

In addition, the entire base 28 is not necessarily made of the pitch-based carbon fiber reinforced resin 42. The base 28 may include the pitch-based carbon fiber reinforced resin 42. Specifically, at least the rear surface 31 of the base 28 may be made of the pitch-based carbon fiber reinforced resin 42.

Second Embodiment

Figure 6:
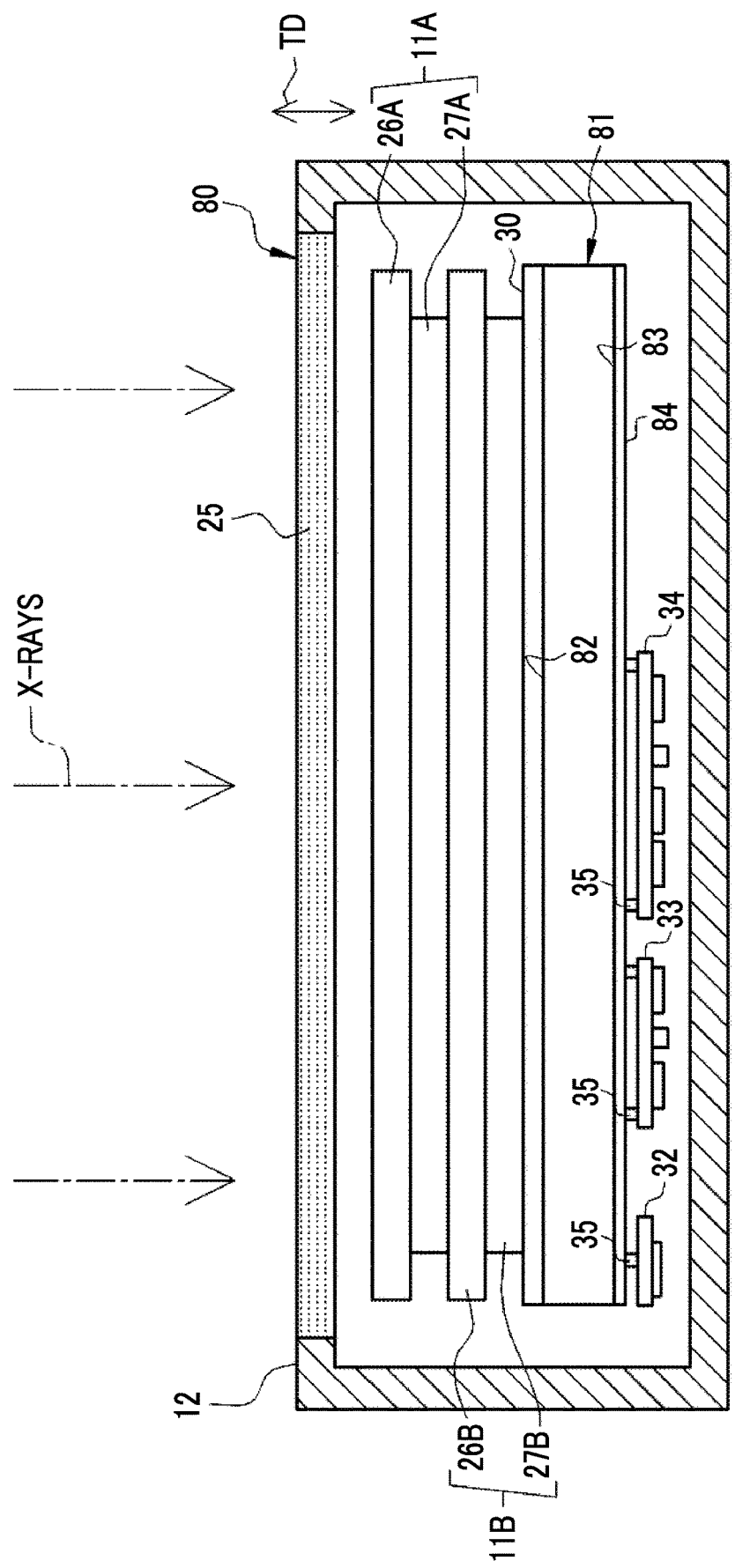
FIG. 6 is a diagram illustrating the internal structure of an electronic cassette according to a second embodiment.

An electronic cassette 80 according to a second embodiment illustrated in FIG. 6 is the same as the electronic cassette 10 according to the first embodiment illustrated in FIG. 2 in, for example, the configuration of the first and second sensor panels 11A and 11B and the structure in which the first and second sensor panels 11A and 11B are attached to a front surface 82 of a base 81 through the heat insulating member 30. The electronic cassette 80 differs from the electronic cassette 10 in that a sheet 84 is attached to a rear surface 83 of the base 81.

The base 81 is not made of the same pitch-based carbon fiber reinforced resin as that forming the base 28 according to the first embodiment and is made of, for example, stainless steel. Instead, the sheet 84 is made of a pitch-based carbon fiber reinforced resin obtained by impregnating a pitch-based carbon fiber with a matrix resin, similarly to the base 28 according to the first embodiment. The fiber directions FD of the pitch-based carbon fibers in the sheet 84 are aligned with one direction, which is not illustrated in the drawings. In addition, the circuit substrates 32 to 34 are arranged such that the long side directions LD thereof are perpendicular to the direction DTC which is parallel to the fiber direction FD and in which thermal conductivity is high. Further, thermal conductivity increases in a direction from a high-density region to a low-density region or from a high-temperature region to a low-temperature region.

As such, unlike the base 28 according to the first embodiment, the base may not be made of the pitch-based carbon fiber reinforced resin and the sheet made of the pitch-based carbon fiber reinforced resin may be attached to the rear surface of the base to impart anisotropy to thermal conductivity in at least the rear surface of the base as in the base 81 according to this embodiment.

In each of the above-described embodiments, the fiber directions FD of the pitch-based carbon fibers are aligned with each other to impart anisotropy to the thermal conductivity of the base. However, the invention is not limited thereto. Anisotropy may be imparted to the thermal conductivity of the base by the following methods illustrated in, for example, FIGS. 7 to 10.

Figure 7:
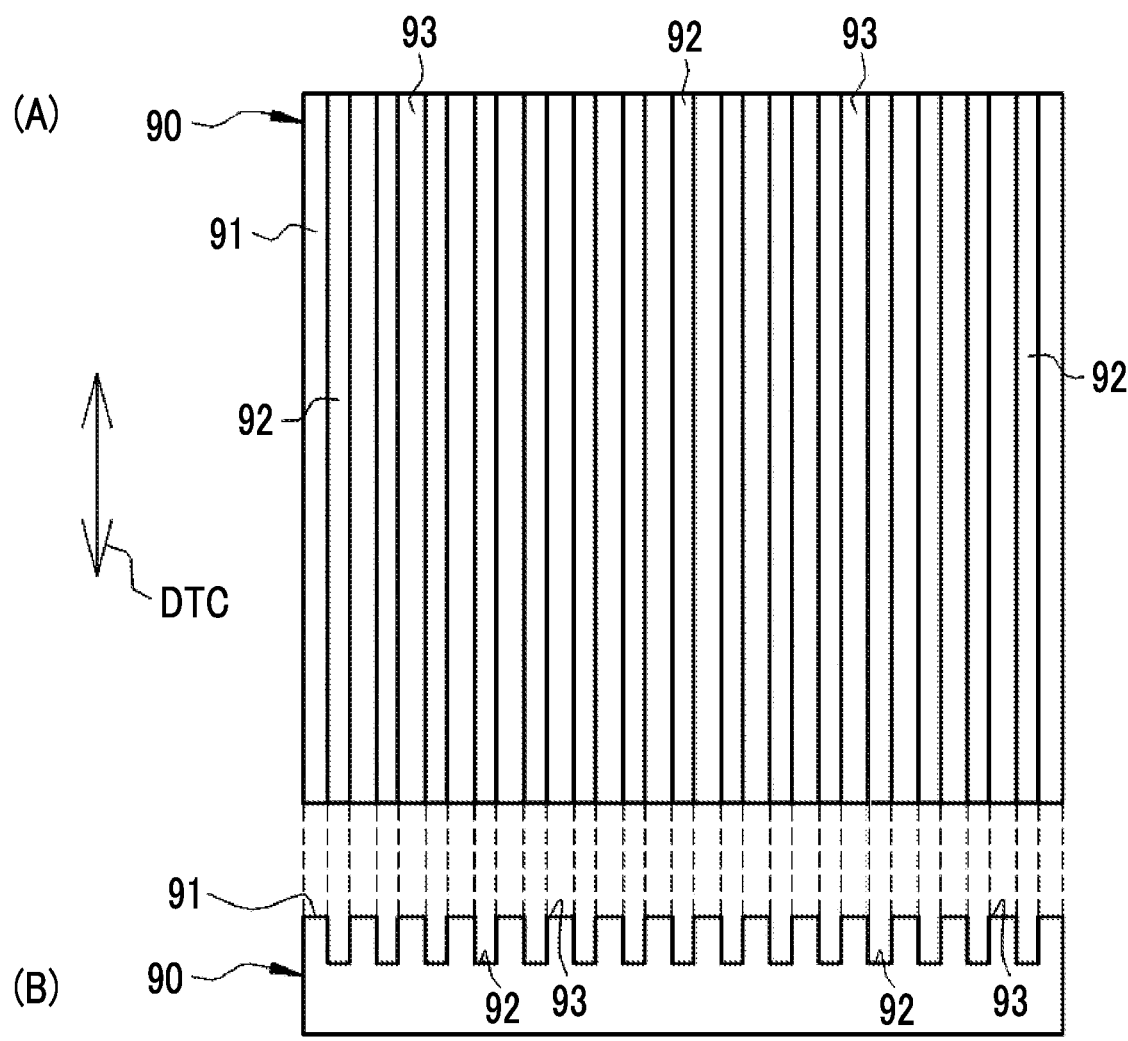
FIG. 7 is a diagram illustrating an example in which grooves are formed in a rear surface of a base and anisotropy is imparted to the thermal conductivity of the base. (A) of FIG. 7 is a plan view illustrating the rear surface of the base and (B) of FIG. 7 is a side view illustrating the base.

In a base 90 illustrated in FIG. 7, a plurality of grooves 92 are formed in a stripe shape in a rear surface 91. Since the grooves 92 cut off a thermal conduction path in a direction perpendicular to the direction in which the grooves 92 extend, heat is unlikely to be transferred. In contrast, since a portion 93 between adjacent grooves 92 functions as the thermal conduction path in the direction DTC parallel to the direction in which the grooves 92 extend, heat is likely to be transferred. That is, in the base 90, thermal conductivity in the direction DTC is increased by the grooves 92 and anisotropy is imparted to thermal conductivity.

Figure 8:
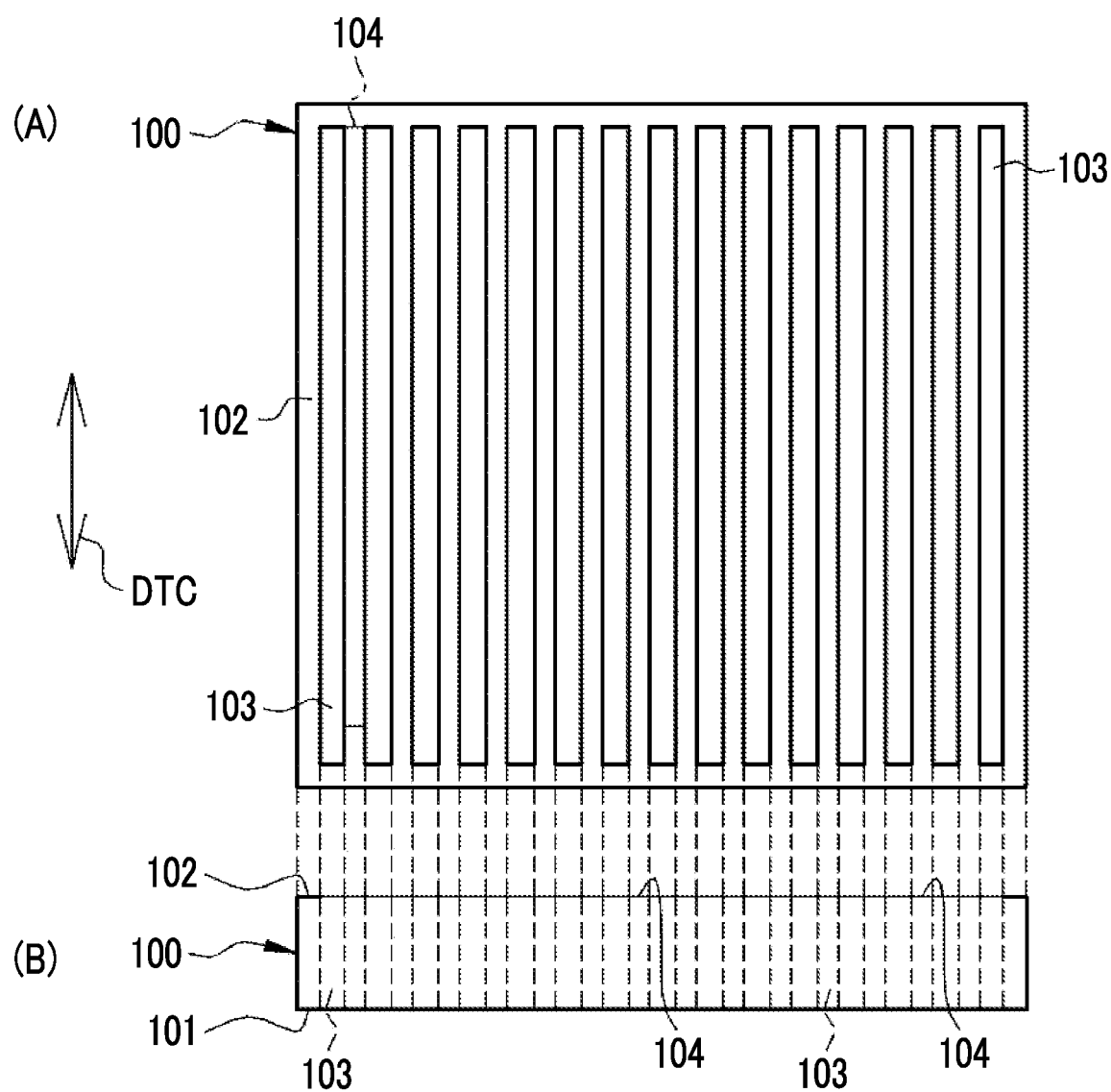
FIG. 8 is a diagram illustrating an example in which slits are formed in a base and anisotropy is imparted to the thermal conductivity of the base. (A) of FIG. 8 is a plan view illustrating the rear surface of the base and (B) of FIG. 8 is a side view illustrating the base.

A base 100 illustrated in FIG. 8 has a one-dimensional lattice shape in which a plurality of slits 103 that have the same width and pass through the base 100 from a front surface 101 to a rear surface 102 are formed at equal intervals. Similarly to the grooves 92 illustrated in FIG. 7, since the slits 103 cut off a thermal conduction path in a direction perpendicular to the direction in which the slits 103 extend, heat is unlikely to be transferred. In contrast, since a joint portion 104 between adjacent slits 103 functions as the thermal conduction path in the direction DTC parallel to the direction in which the slits 103 extend, heat is likely to be transferred. That is, in the base 100, thermal conductivity in the direction DTC is increased by the slits 103 and anisotropy is imparted to thermal conductivity.

Figure 9:
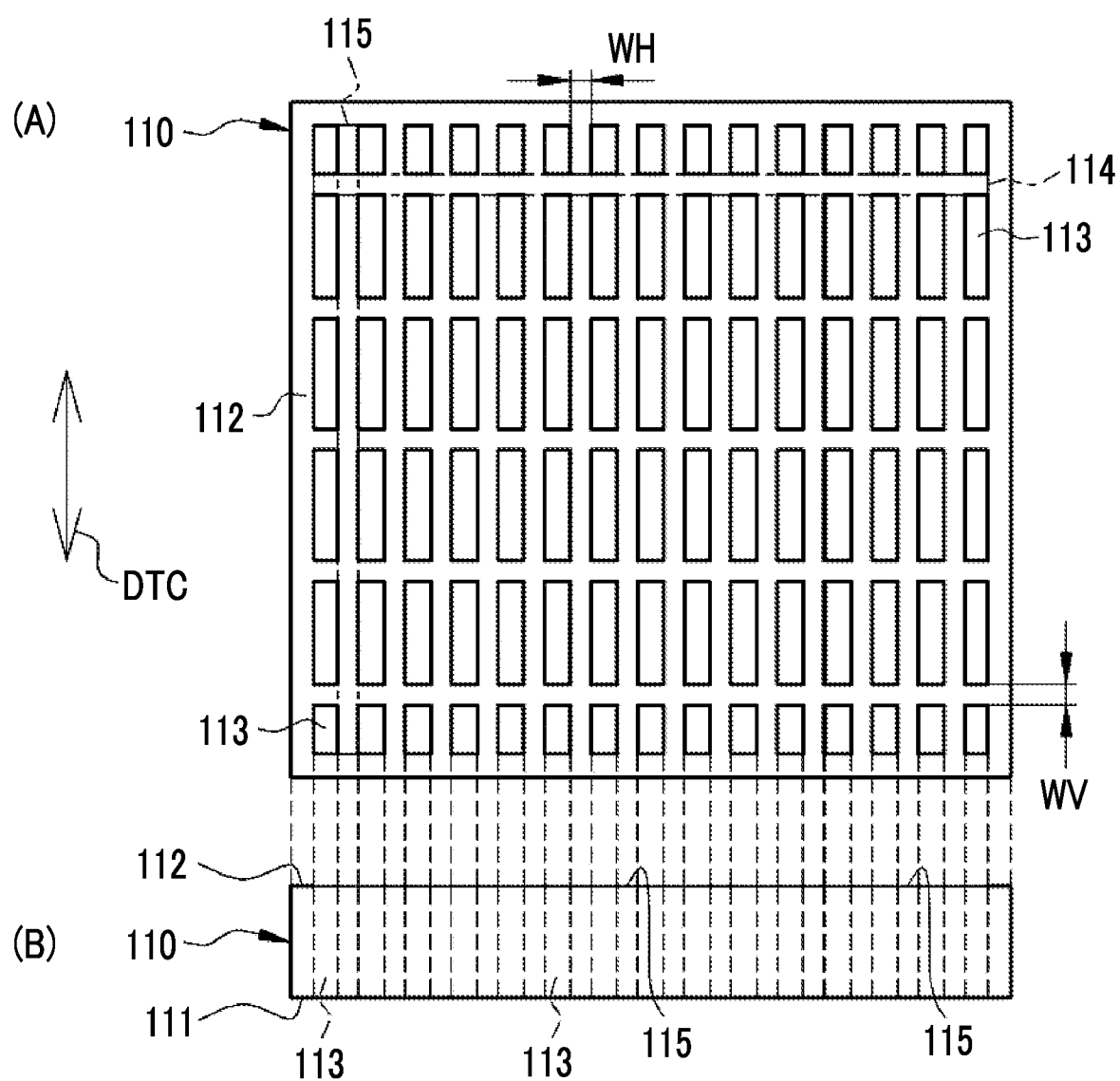
FIG. 9 is a diagram illustrating another example in which slits are formed in a base and anisotropy is imparted to the thermal conductivity of the base. (A) of FIG. 9 is a plan view illustrating the rear surface of the base and (B) of FIG. 9 is a side view illustrating the base.

A base 110 illustrated in FIG. 9 has a two-dimensional lattice shape (mesh shape), as compared to the base 100 having the one-dimensional lattice shape illustrated in FIG. 8. Slits 113 are the same as the slits 103 illustrated in FIG. 8 in that they pass through the base 100 from a front surface 111 to a rear surface 112, have the same width, and are formed at equal intervals.

However, the slit 113 is cut in the direction DTC by a joint portion 114 along a direction perpendicular to the direction DTC parallel to the direction in which the slits 113 extend. Specifically, the slit 113 is divided into six equal parts in the direction DTC by five joint portions 114. The number of joint portions 114 is smaller than 14 which is the number of joint portions 115 between adjacent slits 113 counted along a direction perpendicular to the direction DTC. The widths WV and WH of the joint portions 114 and 115 are equal to each other. Therefore, heat is more likely to be transferred through a thermal conduction path along the direction DTC which is formed by the joint portion 115 than through a thermal conduction path along a direction perpendicular to the direction DTC which is formed by the joint portion 114. Therefore, in the base 110, thermal conductivity in the direction DTC is high and anisotropy is imparted to thermal conductivity. In addition, since the joint portion 114 is provided, the mechanical strength of the base 110 is higher than that of the base 100 illustrated in FIG. 8.

In the base 110 illustrated in FIG. 9, in addition to or instead of the configuration in which the number of joint portions 114 is less than the number of joint portions 115, the width WH of the joint portion 115 may be greater than the width WV of the joint portion 114.

Figure 10:
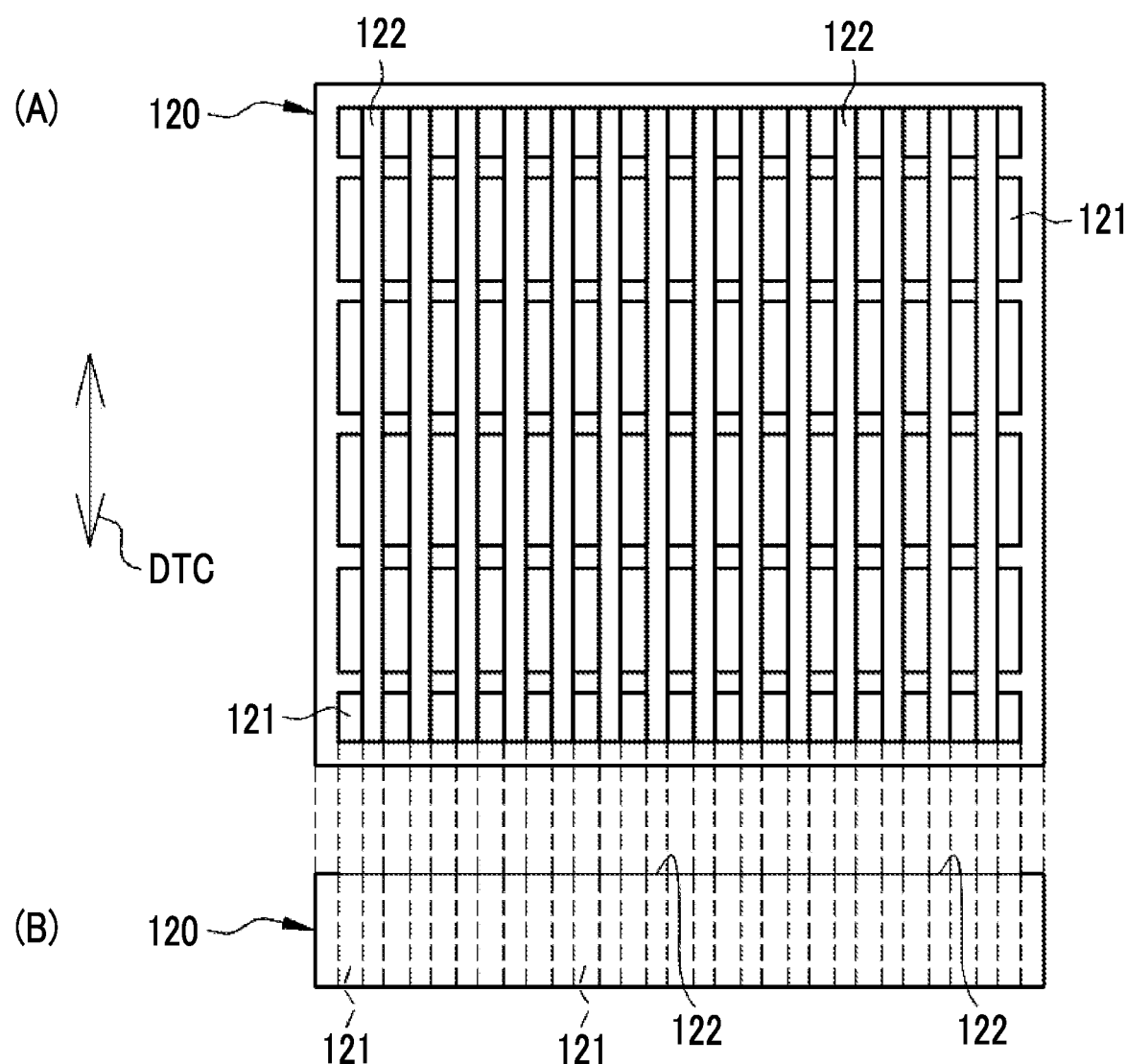
FIG. 10 is a diagram illustrating still another example in which slits are formed in a base and anisotropy is imparted to the thermal conductivity of the base. (A) of FIG. 10 is a plan view illustrating the rear surface of the base and (B) of FIG. 10 is a side view illustrating the base.

Furthermore, as in a base 120 illustrated in FIG. 10, a joint portion 122 between adjacent slits 121 along the direction DTC may be made of a material having a higher thermal conductivity than materials forming other portions. For example, the joint portion 122 is made of copper and the other portions are made of stainless steel. In this case, it is possible to further increase thermal conductivity in the direction DTC.

As such, various methods can be used to impart anisotropy to the thermal conductivity of the base. In the cases illustrated in FIGS. 7 to 10, the circuit substrates are provided such that the long side directions LD thereof are perpendicular to the direction DTC, which is not illustrated in the drawings. In addition, thermal conductivity increases in the direction from a high-density region to a low-density region or from a high-temperature region to a low-temperature region.

Figure 11:
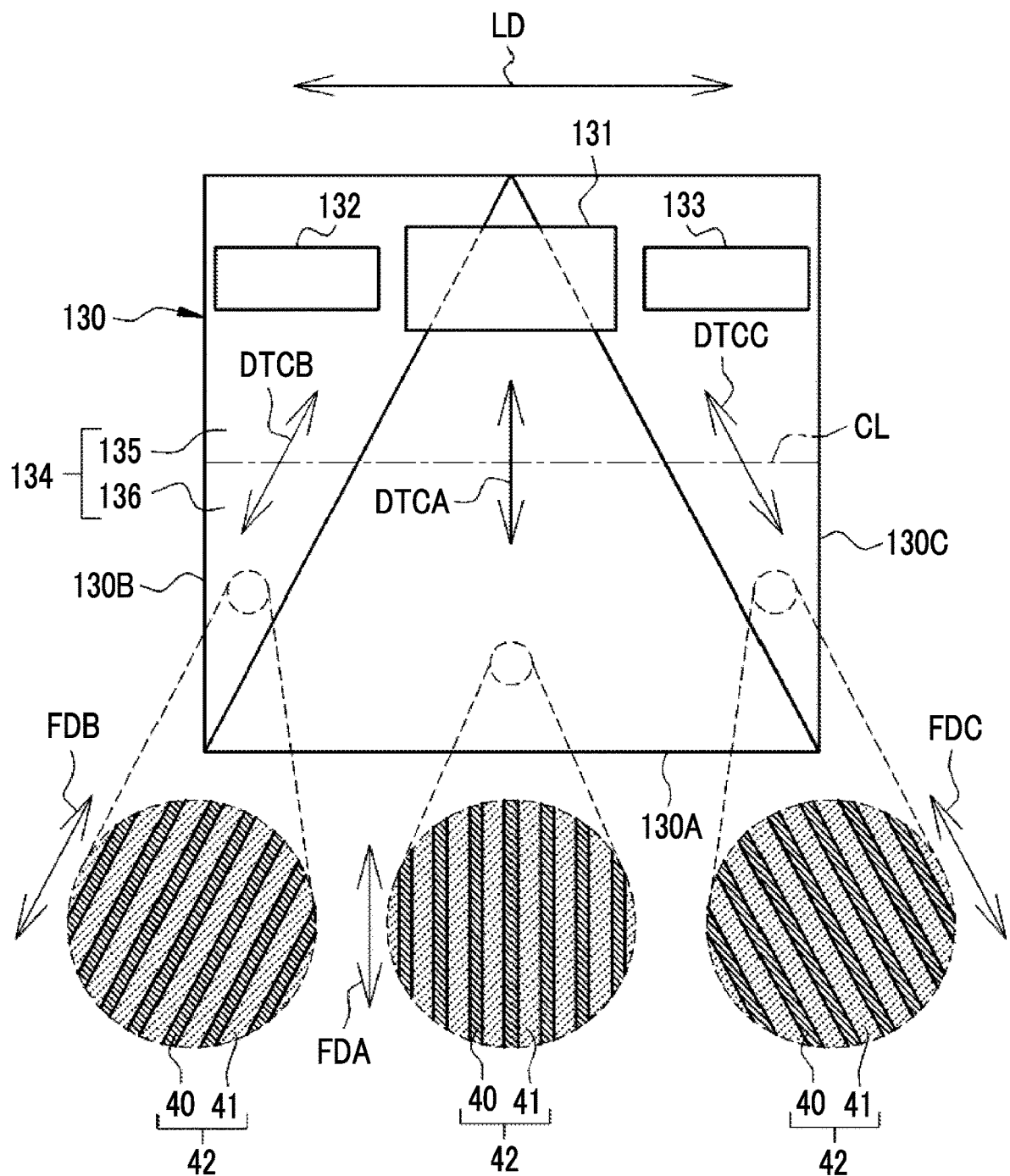
FIG. 11 is a diagram illustrating an example in which a direction in which thermal conductivity is high is changed in each region of the rear surface and is inclined with respect to the side of the base.

As in a base 130 illustrated in FIG. 11, the direction DTC in which thermal conductivity is high may be changed in each region of the rear surface of the base. In addition, the direction DTC in which thermal conductivity is high may be inclined with respect to the side of the base.

In FIG. 11, the base 130 is formed by bonding three blocks 130A, 130B, and 130C having a triangular shape in a plan view. The block 130A is provided in a central portion of the base 130 and the blocks 130B and 130C are symmetrically provided on the left and right sides of the block 130A.

Circuit substrates 131, 132, and 133 are provided such that they are biased to one side (the upper side in FIG. 11) of a rear surface 134 and are close to each other. The circuit substrate 131 is provided over the blocks 130A to 130C. The circuit substrate 132 is provided in the block 130B and the circuit substrate 133 is provided in the block 130C.

The rear surface 134 of the base 130 is divided into two equal regions, that is, a high-density and high-temperature region 135 and a low-density and low-temperature region 136 by a center line CL represented by a one-dot chain line as in the first embodiment.

In the block 130A, a direction DTCA in which thermal conductivity is high is parallel to the side of the base 130. In contrast, in the blocks 130B and 130C, directions DTCB and DTCC in which thermal conductivity is high are inclined with respect to the side of the base 130. Specifically, the directions DTCB and DTCC are directions from the high-density and high-temperature region 135 to the low-density and low-temperature region 136 and are inclined outward. In the blocks 130A to 130C, the fiber directions FDA, FDB, and FDC of pitch-based carbon fibers 40 are changed as illustrated in dashed circles such that the directions DTCA, DTCB, and DTCC in which thermal conductivity is high are different from each other.

As such, the direction DTC in which thermal conductivity is high may be changed in each region of the rear surface of the base or may be inclined with respect to the side of the base. In addition, not only the direction DTCA in which thermal conductivity is high in the block 130A, but also the directions DTCB and DTCC in which thermal conductivity is high in the blocks 130B and 130C are inclined with respect to the side of the substrate and there is no difference in the direction from the high-density and high-temperature region 135 to the low-density and low-temperature region 136. Therefore, in the rear surface 134, thermal conductivity is high in the direction from the high-density region to the low-density region and is high in the direction from the high-temperature region to the low-temperature region.

The direction DTC in which thermal conductivity is high may be changed in each region of the rear surface of the base or the direction DTC in which thermal conductivity is high may be inclined with respect to the side of the base by, for example, changing the attachment direction of the sheet 84 made of the pitch-based carbon fiber reinforced resin, by changing the extension direction of the grooves 92 illustrated in FIG. 7, or by changing the extension direction of the slits 103, 113, and 121 illustrated in FIGS. 8 to 10 in the second embodiment.

Figure 12:
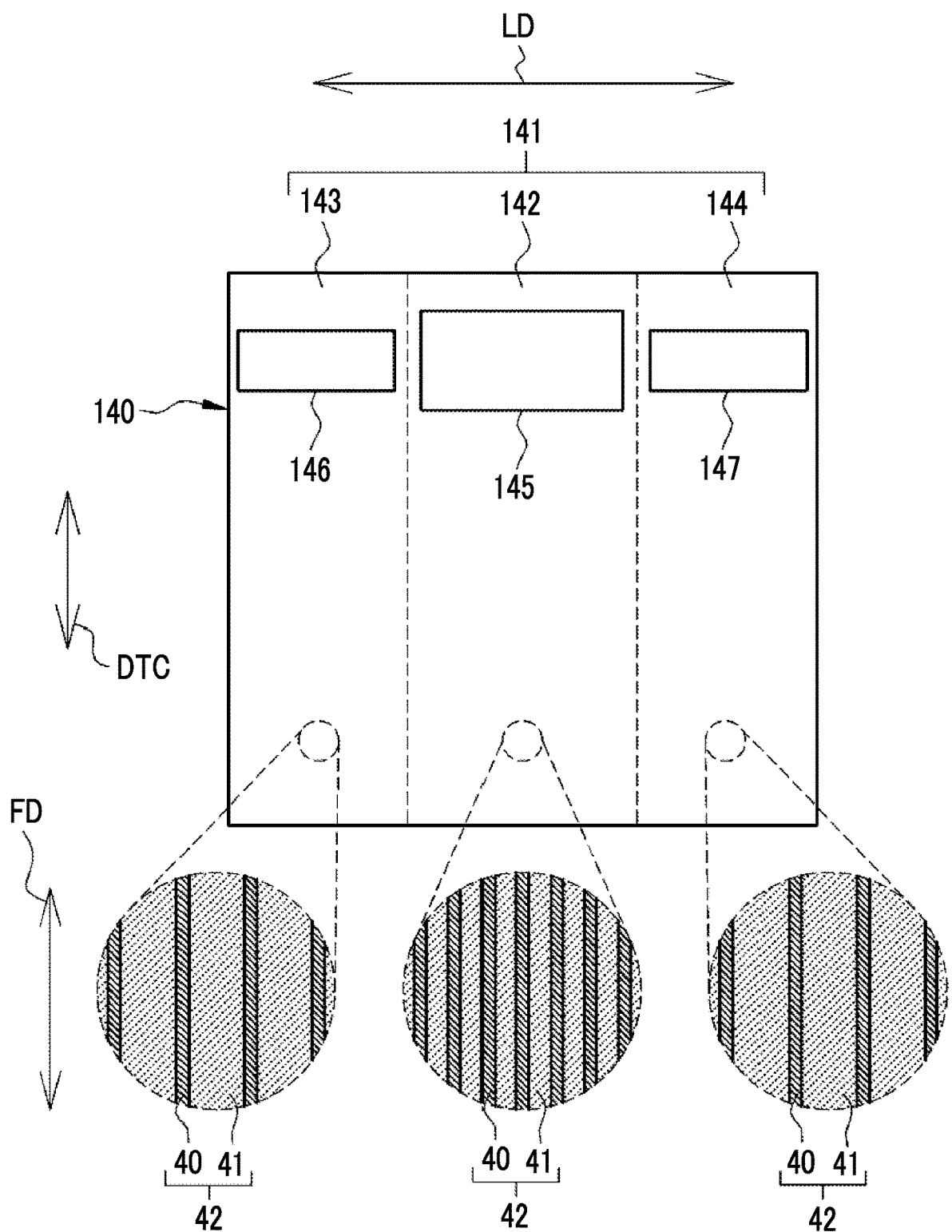
FIG. 12 is a diagram illustrating an example in which thermal conductivity is changed in each region of the rear surface of the base.

As in a base 140 illustrated in FIG. 12, a rear surface 141 may be divided into a plurality of regions 142, 143, and 144 and thermal conductivity in each of the regions 142 to 144 may be changed.

In the base 140, the density of the pitch-based carbon fibers 40 in each of the regions 142 to 144 is changed to change thermal conductivity in each of the regions 142 to 144. Specifically, the density of the pitch-based carbon fibers 40 in the center region 142 is higher than that in the left and right regions 143 and 144. Therefore, the thermal conductivity of the region 142 is higher than the thermal conductivity of the regions 143 and 144.

In this case, a circuit substrate 145 that generates a relatively large amount of heat is provided in the region 142 with high thermal conductivity and circuit substrates 146 and 147 that generate a relatively small amount of heat are provided in the regions 143 and 144 with low thermal conductivity. Therefore, it is possible to more actively diffuse the driving heat of the circuit substrate 145 that generates a relatively large amount of heat.

FIG. 12 illustrates an example in which the base 140 is made of the pitch-based carbon fiber reinforced resin 42. However, the invention may be applied to the sheet 84 made of a pitch-based carbon fiber reinforced resin in the second embodiment.

In addition, the invention may be applied to the grooves 92 illustrated in FIG. 7. In this case, the number of grooves 92 in a region in which thermal conductivity is desired to increase is less than that in a region in which thermal conductivity is desired to decrease. Alternatively, the width of the portion 93 between adjacent grooves 92 in the region in which thermal conductivity is desired to increase is greater than that in the region in which thermal conductivity is desired to decrease. In addition, the invention may be applied to the slits 103, 113, and 121 illustrated in FIGS. 8 to 10. In this case, the number of joint portions 104, 115, and 122 in the region in which thermal conductivity is desired to increase is greater than that in the region in which thermal conductivity is desired to decrease. Alternatively, the width of adjacent joint portions 104, 115, and 122 in the region in which thermal conductivity is desired to increase is greater than that in the region in which thermal conductivity is desired to decrease.

All of the circuit substrates may not be provided such that the long side directions LD thereof are perpendicular to the direction DTC. The circuit substrate that is provided such that the long side direction LD thereof is perpendicular to the direction DTC may be, for example, only a circuit substrate having a long side whose length is equal to or greater than a quarter of the side of the base along the long side direction or only a circuit substrate that at least generates the largest amount of heat among all of the circuit substrates.

The case in which the center line demarcating the high-density region and the low-density region is aligned with the center line demarcating the high-temperature region and the low-temperature region has been described. However, it is also considered that the center line demarcating the high-density region and the low-density region is perpendicular to the center line demarcating the high-temperature region and the low-temperature region, depending on the layout of the circuit substrates. In this case, the direction DTC in which thermal conductivity is high is the direction from the high-temperature region to the low-temperature region.

The circuit substrate mounted on the rear surface of the base is not limited to a rectangular shape in a plan view. For example, the circuit substrate may have a square shape in a plan view or may have a polygonal shape, a circular shape, or an elliptical shape in a plan view.

Here, the terms "rectangular shape" "square shape", "polygonal shape", "circular shape", and "elliptic shape", indicate that the overall contour of the circuit substrate follows the shapes. Therefore, the shapes include a case in which a circuit substrate is partially removed, such as a case in which four corners of a circuit substrate having a rectangular outline as a whole are chamfered or a case in which a central portion of a circular circuit substrate is hollowed out.

The state in which "two sensor panels are sequentially arranged in the thickness direction" is not limited to the state in which two sensor panels are closely arranged as in each of the above-described embodiments. The state in which "two sensor panels are sequentially arranged in the thickness direction" also includes a state in which two sensor panels are not closely arranged and are separated from each other with a gap therebetween and a state in which an insert, such as an X-ray filter for restricting the incidence of soft ray components of X-rays, is interposed between two sensor panels.

In each of the above-described embodiments, the electronic cassette in which two sensor panels 11A and 11B are sequentially arranged in the thickness direction TD is given as an example. However, the invention is not limited thereto. The invention can also be applied to an electronic cassette including one sensor panel.

In each of the above-described embodiments, the electronic cassette is given as an example of the radiographic image detection device. However, the invention is not limited thereto. The invention can also be applied to a stationary radiographic image detection device that is fixed to the imaging table. In addition, the invention is not limited to X-rays and can also be applied to a case in which other types of radiation, such as γ-rays, are used.

The conjunction "or" described in the specification is not an expression intended to be a limited interpretation of any one of a plurality of options connected by the conjunction depending on the context, but is an expression including combinations of the plurality of options. For example, a sentence "an option A or an option B is performed" needs to be interpreted as having the following three meanings, depending on the context: "an option A is performed"; "an option B is performed"; and "an option A and an option B are performed".

The invention is not limited to each of the above-described embodiments and various configurations may be used as long as they do not depart from the scope and spirit of the invention.

EXPLANATION OF REFERENCES 10, 80: electronic cassette (radiographic image detection device)
11A: first sensor panel
11B: second sensor panel
12: housing
13: imaging table
14: holder
15: X-ray source (radiation source)
16: console
17: display
18: input device
25: transmission plate
26A, 26B: first, second light detection substrate
27A, 27B: first, second scintillator
28, 81, 90, 100, 110, 120, 130, 140: base
29, 82, 101, 111: front surface of base
30: heat insulating member
31, 83, 91, 102, 112, 134, 141: rear surface of base
32 to 34, 131 to 133, 145 to 147: circuit substrate
35: spacer
40: pitch-based carbon fiber
41: matrix resin
42: pitch-based carbon fiber reinforced resin
45, 135: high-density and high-temperature region
46, 136: low-density and low-temperature region
50A, 50B: first and second pixels
51A, 51B: first and second gate lines
52A, 52B: first and second signal lines
53A, 53B: first and second photoelectric conversion units
54A, 54B: first and second TFTs
60A, 60B: first and second circuit units
61A, 61B: first and second gate driving circuits
62A, 62B: first and second signal processing circuits
63: control circuit
64: power supply unit
70: ES image generation unit
71: bone density calculation unit
84: sheet made of pitch-based carbon fiber reinforced resin
92: groove
93: portion between adjacent grooves
103, 113, 121: slit
104, 115, 122: joint portion along direction in which slit extends
114: joint portion along direction perpendicular to direction parallel to direction in which slit extends
130A to 130C: block
142 to 144: region
H: subject
TD: thickness direction
LD: long side direction of circuit substrate
SD: short side direction of circuit substrate
L1 to L3: length of long side of circuit substrate
L4: length of side of base along long side direction of circuit substrate
FD, FDA to FDC: fiber direction of pitch-based carbon fiber
DTC, DTCA to DTCC: direction in which thermal conductivity is high
X: row direction of pixel
Y: column direction of pixel
WV: width of joint portion along direction perpendicular to direction parallel to direction in which slit extends
WH: width of joint portion along direction in which slit extends

What is claimed is:

1. A radiographic image detection device comprising:
a sensor panel in which pixels that accumulate charge in response to radiation, which has been emitted from a radiation source and transmitted through a subject, are two-dimensionally arranged;
a circuit unit that converts the charge into a digital signal, outputs the digital signal as a radiographic image, and includes a plurality of circuit substrates on which various circuits are mounted; and
a base that has a front surface to which the sensor panel is attached and a rear surface on which the circuit substrates are mounted and has anisotropic thermal conductivity in at least the rear surface.

2. The radiographic image detection device according to claim 1,
wherein at least one of the plurality of circuit substrates has a rectangular shape in a plan view and is provided such that a long side direction is perpendicular to a direction in which thermal conductivity is high in the rear surface.

3. The radiographic image detection device according to claim 2,
wherein a length of a long side of the circuit substrate is equal to or greater than a quarter of a length of a side of the base along the long side direction.

4. The radiographic image detection device according to claim 1,
wherein the rear surface is divided into two equal regions, that is, a high-density region in which mounting density of the circuit substrates is relatively high and a low-density region in which the mounting density of the circuit substrates is relatively low,
the circuit substrates are provided in the high-density region and the low-density region, and
in the rear surface, thermal conductivity in a direction from the high-density region to the low-density region is high.

5. The radiographic image detection device according to claim 1,
wherein the rear surface is divided into two equal regions, that is, a high-temperature region in which an amount of heat generated from the circuit substrates is relatively large and a low-temperature region in which the amount of heat generated from the circuit substrates is relatively small,
the circuit substrates are provided in the high-temperature region and the low-temperature region, and
in the rear surface, thermal conductivity in a direction from the high-temperature region to the low-temperature region is high.

6. The radiographic image detection device according to claim 1,
wherein the base includes a pitch-based carbon fiber reinforced resin obtained by impregnating a pitch-based carbon fiber with a matrix resin.

7. The radiographic image detection device according to claim 6,
wherein at least the rear surface of the base is made of the pitch-based carbon fiber reinforced resin.

8. The radiographic image detection device according to claim 1,
wherein a sheet that is made of a pitch-based carbon fiber reinforced resin obtained by impregnating a pitch-based carbon fiber with a matrix resin is attached to the rear surface of the base.

9. The radiographic image detection device according to claim 6,
wherein fiber directions of the pitch-based carbon fibers are aligned with one direction.

10. The radiographic image detection device according to claim 1,
wherein a heat insulating member is attached to the front surface of the base, and
the sensor panel is attached to the front surface through the heat insulating member.

11. The radiographic image detection device according to claim 1,
wherein two pairs each including the sensor panel and the circuit unit are provided, and
the two sensor panels are sequentially arranged in a thickness direction.

12. The radiographic image detection device according to claim 11,
wherein two radiographic images output from the two circuit units are used to calculate an index value related to bones.

* * * * *